United States Patent [19]

Kojima et al.

[11] 4,009,035
[45] Feb. 22, 1977

[54] PROCESS FOR FORMING CYAN DYE PHOTOGRAPHIC IMAGES

[75] Inventors: Tamotsu Kojima; Shui Sato; Takaya Endo; Tugumoto Usui; Tomio Horiuchi, all of Hino, Japan

[73] Assignee: Konishiroku Photo Industry Co., Ltd., Tokyo, Japan

[22] Filed: Jan. 22, 1975

[21] Appl. No.: 543,044

[30] Foreign Application Priority Data

Jan. 25, 1974 Japan ............................. 49-10787

[52] U.S. Cl. .................................. 96/55; 96/100
[51] Int. Cl.$^2$ .................... G03C 7/00; G03C 1/40
[58] Field of Search ................................ 96/100, 55

[56] References Cited

UNITED STATES PATENTS

| | | | |
|---|---|---|---|
| 2,895,826 | 7/1959 | Salminen et al. | 96/100 |
| 3,462,270 | 8/1969 | Eynde et al. | 96/100 |
| 3,758,308 | 9/1973 | Beavers et al. | 96/100 |
| 3,779,763 | 12/1973 | Lau | 96/100 |

*Primary Examiner*—J. Travis Brown
*Attorney, Agent, or Firm*—Haseltine, Lake & Waters

[57] ABSTRACT

A cyan coupler of the formula $A - NHCO(CF_2CF_2)_nH$ wherein A is a phenolic or naphtholic cyan coupler residue and $n$ is a positive integer of 1 to 7, incorporated in a light-sensitive silver halide photographic material produces a cyan dye photographic image which is favorable in light absorption characteristics and excellent in fastness when the coupler is developed with an aromatic primary amine type developing agent.

3 Claims, No Drawings

PROCESS FOR FORMING CYAN DYE PHOTOGRAPHIC IMAGES

This invention relates to a process for forming a cyan dye photographic image. More particularly, the invention is concerned with a process for forming a cyan dye photographic image, which is favorable in light absorption characteristic and excellent in fastness, by subjecting a light-sensitive silver halide photographic material to color development with an aromatic primary amine type developing agent in the presence of a novel cyan coupler.

Generally, the formation of a color photographic image according to subtractive color photography is carried out by subjecting a light-sensitive silver halide color photographic material to color development by use of an aromatic primary amine type developing agent in the presence of cyan, magenta and yellow couplers. In this case, silver halide particles of the photographic material, which have been exposed to light, are reduced by means of the developing agent, and the oxidation product of the developing agent, which has been formed at the same time, couples with the couplers to give a color photographic image composed of cyan, magenta and yellow dyes.

Each of the above-mentioned couplers may be incorporated into either a silver halide photographic emulsion or a color developer. Generally, a light-sensitive silver halide photographic material, which has been incorporated with the couplers, is called an internal type photographic material, while that which is to be processed with a color developer incorporated with the couplers, is called an incorporated type photographic material.

The cyan dye photographic image of a color photograph has absorbed red light in the wavelength region of about 600 to 700 m$\mu$., and a compound having a phenolic hydroxyl group has been used, in general, as a cyan coupler for forming the cyan dye.

The cyan coupler is preferably a compound which not only forms a cyan dye but also has such various characteristic properties that, for example, it is favorable in color developability, is high in solubility in alkalis, water and organic solvents, is high in dispersibility and stability in silver halide photographic emulsions, and can form a dye which is fast to light, heat, humidity and the like, is capable of light absorption over a desirable wavelength region and is high in transparency and color density.

Although many investigations concerning cyan couplers having the above-mentioned properties have been made hitherto, the actual technical state is such that no desirable cyan coupler capable of satisfying all the above-mentioned characteristic properties has been found yet.

For example, the cyan couplers composed of diacyl aminophenols as disclosed in U.S. Pat. No. 2,772,162 are excellent in that they give cyan dye images which are favorable in various properties including fastness to heat, humidity, etc., but have the disadvantages that the wavelength region for light absorption and absorption maximum of cyan dyes formed therefrom is excessively inclined to the short wavelength side.

On the other hand, the cyan couplers composed of 2-acylamino-6-chloro-5-substituted phenols as disclosed in U.S. Pat. No. 2,423,730 are superior to the above-mentioned couplers composed of diacylaminophenols in that they can form cyan dyes whose light absorption is on the long wavelength side, but have the disadvantage that the cyan dyes are insufficient in fastness to heat, humidity etc.

Further, the cyan couplers having perfluoroalkylcarbonamido groups at the 2-positions of phenol or naphthol nuclei, as disclosed in U.S. Pat. No. 2,895,826, are excellent in that cyan dyes formed therefrom have light absorption on the long wavelength side, high in maximum color density and favorable particularly in light fastness, but are not always satisfactory in solubility in water, alkalis or organic solvents, (e.g. oil-protected dispersion type high boiling organic solvents such as dibutyl phthalate, tricresyl phosphate, etc.) and dispersion stability in photographic emulsions.

In view of the above, the advent of cyan couplers which are superior in said properties has been desired.

An object of the present invention is to provide a novel cyan coupler which has the desirable properties required for cyan couplers as mentioned previously and which is suitable for forming a color photographic image according to subtractive color photography, and to provide a process for forming a cyan dye image desirable for a color photograph by developing a light-sensitive silver halide photographic material in the presence of said cyan coupler.

The above-mentioned object can be accomplished by subjecting a light-sensitive silver halide photographic material to color development using an aromatic primary amine type developing agent in the presence of, as a cyan coupler, a compound having a monohydro-polyfluoroalkylcarbonamido group which is represented by the formula,

$$A-NHCO(CF_2CF_2)_nH$$

wherein A is a phenolic or naphtholic cyan coupler residue, and n is a positive integer of 1 to 7.

The cyan coupler of the above-mentioned general formula (hereinafter referred to as the cyan coupler of the present invention) is characterized by having in its molecular structure a monohydro-polyfluoroalkylcarbonamido group having a hydrogen atom at the terminal, and can display various characteristic properties by virtue of the presence of said group.

That is, the cyan coupler of the present invention is favorable in solubility in water, alkalis and organic solvents, in dispersion stability in photographic emulsions, and in color developability, and gives by color development a cyan dye image which is high in maximum color density, has a light absorption in a desirable range on the long wavelength side, is favorable in transparency and is excellent in fastness to light, heat and humidity.

The cyan coupler of the present invention is particularly excellent in solubility as compared with a cyan coupler incorporated with a perfluoroalkylcarbonamido group, where all the hydrogen atoms of the alkyl group have been substituted by fluorine atoms. The reason therefor is probably that since the polarity of the cyan coupler of the present invention is high due to the presence of one hydrogen atom at the terminal of the fluoroalkyl group, the cyan coupler becomes high in solvation and increases in affinity, with the result that it is high in solubility in water, organic solvents and the like polar solvents. Further, the shorter the chain length of the fluoroalkyl group, i.e. the smaller the value of n in the aforesaid general formula, the higher the polarity of the cyan coupler, and thus there is a tendency that the cyan coupler of the present invention becomes higher in solubility with increasing value of $n$.

On the other hand, a cyan coupler having a perfluoroalkylcarbonamido group has the characteristic of being particularly excellent in heat resistance. The cyan coupler of the present invention has an alkylcarbonamido group in which many fluorine atoms have been substituted, and hence is also excellent in heat resistance, and, in case the structures of other portions are the same, it has been observed that the cyan coupler of the present invention is superior.

In the cyan coupler of the present invention, the position into which the monohydro-polyfluoroalkylcarbonamido group is to be introduced may be optional. However, in order to make the group sufficiently display its action as an electron attractive group and to make the light absorption of the resulting cyan dye present on the desirable long wavelength side, it is preferable to introduce the group directly into the phenol or naphthol nucleus of the cyan coupler. It is needless to say that if sufficient electron attractivity has been imparted to the cyan coupler, the said group is not required to be introduced directly into said nucleus but may be introduced through a proper linking group.

The cyan couplers of the present invention include those which are soluble in water, alkalis or oils, and those of the internal type which are to be incorporated into silver halide photographic emulsions and of the incorporated type which are to be incorporated into color developers, and the kinds thereof are decided according to the kinds of groups which are introduced into the phenol or naphthol nuclei.

Typical examples of the cyan couplers of the present invention are shown below.

Coupler (1)

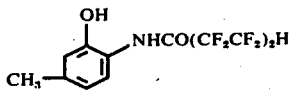

Coupler (2)

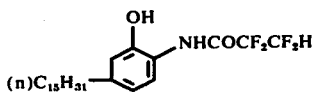

Coupler (3)

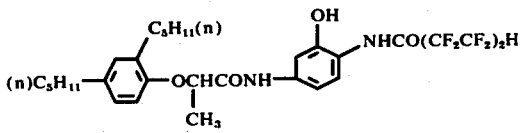

Coupler (4)

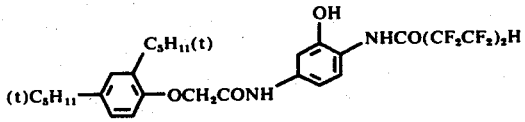

Coupler (5)

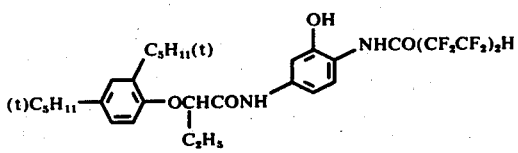

Coupler (6)

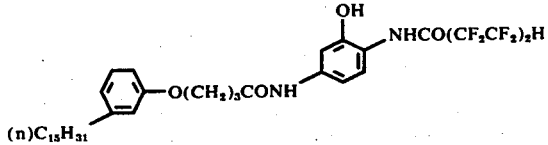

Coupler (7)

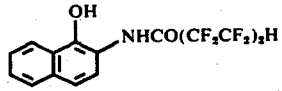

Coupler (8)

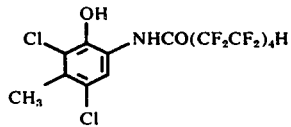
Coupler (9)
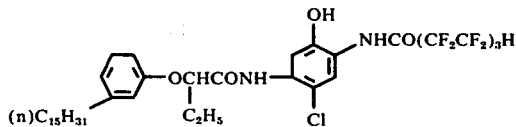
Coupler (10)
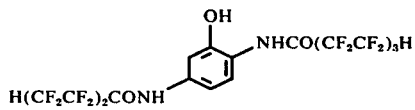
Coupler (11)
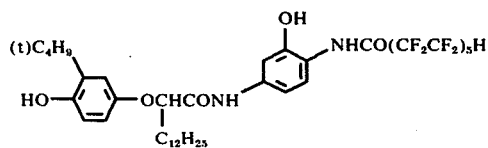
Coupler (12)
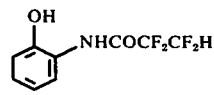
Coupler (13)
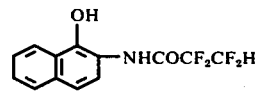
Coupler (14)
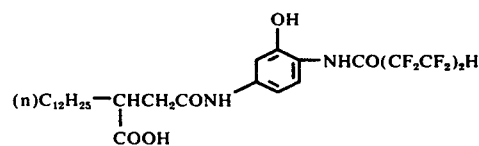
Coupler (15)
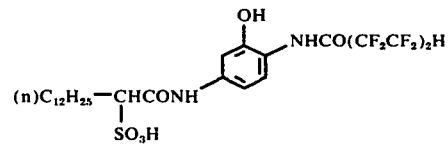
Coupler (16)
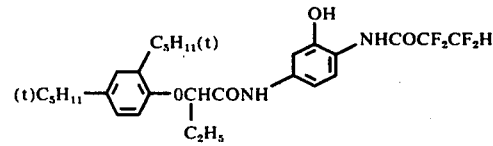
Coupler (17)
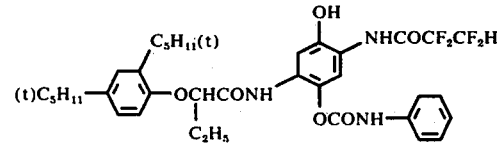
Coupler (18)

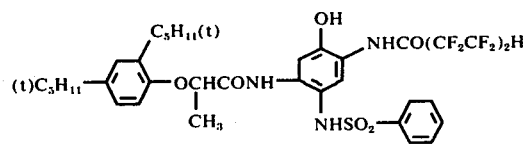
Coupler (19)
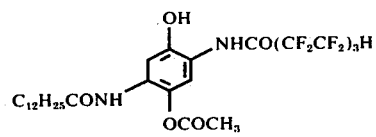
Coupler (20)
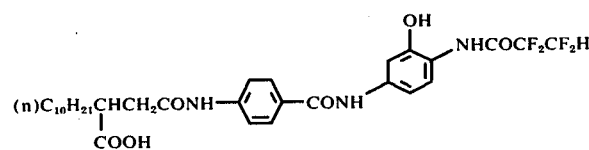
Coupler (21)
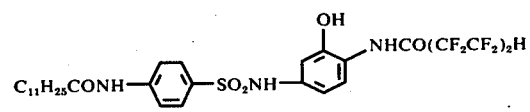
Coupler (22)
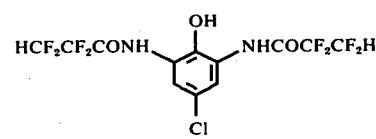
Coupler (23)
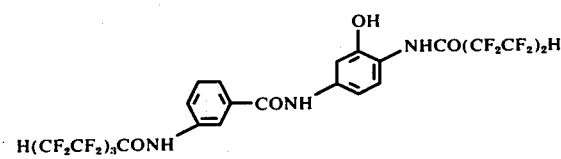
Coupler (24)
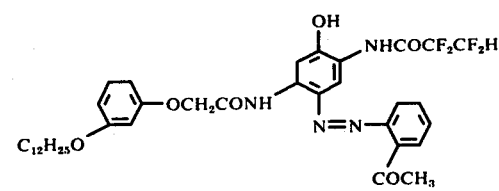
Coupler (25)
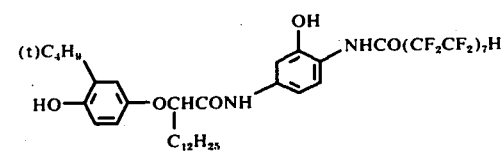
Coupler (26)
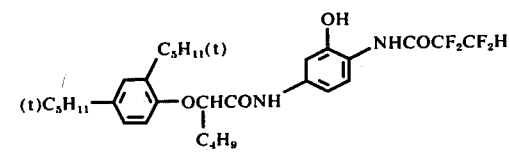
Coupler (27)

-continued

Procedures for synthesizing typical cyan couplers of the present invention are explained below with reference to synthesis examples.

SYNTHESIS EXAMPLE 1

Synthesis of 2-(ω-monohydro-octafluoropentanoylamino)-5-[α-(2,4-di-tert-amylphenoxy)-butyramide]phenol [Coupler (5)]

(1)-1. Synthesis of ω-monohydro-octafluoropentanoyl chloride

48 Grams of ω-monohydro-octafluoropentanoic acid (synthesized according to the method disclosed in U.S. Pat. No. 2,559,629) is gradually added dropwise to 42 g. of phosphorus pentachloride, and the resulting mixture is reacted at 90° C. ± 10° C. for 1 hour, whereby a colorless transparent liquid reaction mixture is obtained. This reaction mixture is distilled at atmospheric pressure to obtain 34 g. of the end product which is a colorless liquid having a boiling point of 89° to 93° C.

(1)-2. Synthesis of 2-(ω-monohydro-octafluoropentanoylamino)-5-nitrophenol

27 Grams of the ω-monohydro-octafluoropentanoyl chloride obtained in the above-mentioned step (1)-1 is gradually added to a solution comprising 15 g. of 2-amino-5-nitrophenol, 100 ml. of dioxane and 26 g. of quinoline, and the resulting mixture is stirred at room temperature for 7 hours. Subsequently, the liquid reaction mixture is poured into a dilute aqueous hydrochloric acid solution to deposit yellow precipitates, which are then collected by filtration, washed with water and dried, whereby a crude product is obtained. This crude product is recrystallized from 150 ml. of benzene to obtain the end product consisting of yellow crystals having a melting point of 127° to 130° C.

(1)-3. Synthesis of 2-(ω-monohydro-octafluoropentanoylamino)-5-aminophenol

A solution of 38 g. of the 2-(ω-monohydro-octafluoropentanoylamino)-5-nitrophenol obtained in the aforesaid step (1)-2 in 400 of methyl alcohol is incorporated with 4 g. of a palladium-carbon catalyst, and then subjected to catalytic hydrogenation under pressure (3 atm.) at 70° C. for 5 hours. Thereafter, the liquid reaction mixture is freed by filtration from the catalyst, and the filtrate is heated to dryness under reduced pressure to obtain 32 g. of the end product which is a pale yellow resinous substance.

(1)-4. Synthesis of 2-(ω-monohydro-octafluoropentanoylamino)-5-[α-(2,4-di-tert-amylphenoxy)-butyramide]phenol [Coupler (5)]

To a solution comprising 35 g. of the 2-(ω-monohydro-octafluoropentanoylamino)-5-aminophenol obtained in the above-mentioned step (1)-3, 100 ml. of dioxane and 26 g. of quinoline is added a solution of 34 g. of α-(2,4-di-tert-aminophenoxy)butyroyl chloride in 50 ml. of dioxane, and the resulting mixture is reacted with stirring at room temperature for 7 hours. Thereafter, the liquid reaction mixture is poured into a dilute aqueous hydrochloric acid solution to deposit precipitate, which is then collected by filtration, washed with water and dried, whereby a crude product is obtained. This crude product is recrystallized from 350 ml. of hexane to obtain 40 g. of the end product consisting of white powdery crystals having a melting point of 95° to 98° C.

SYNTHESIS EXAMPLE 2

Synthesis of 2-(ω-monohydro-octafluoropentanoylamino)-5-[α-(2,4-di-tert-amylphenoxy)acetamino]phenol [Coupler (4)]

Synthesis Example 1 was repeated, except that the α-(2,4-di-tert-amylphenoxy)butyroyl chloride obtained in the step (1)-4 is replaced by α-(2,4-di-tert-amylphenoxy)acetyl chloride and that the crude product is recrystallized from 180 ml. of acetonitrile, to obtain 44 g. of the end product consisting of white fine crystalline needles having a melting point of 182° to 185° C.

As mentioned previously, the cyan couplers of the present invention include those which are soluble in water, alkalis and oils. Among the water- and alkali-soluble cyan couplers, those which are of the type having diffusion-preventing groups can be dispersed and incorporated according to the so-called Fischer's dispersion method into silver halide photograhpic emulsions. Examples of the cyan couplers belonging to this type are the aforesaid couplers (14), (15) and (20). On the other hand, those which are of the type having no diffusion-preventing groups are incorporated into color developers and can be used for the processing of light-sensitive silver halide color photographic materials of the incorporated type. Examples of the cyan couplers belonging to this type are the aforesaid couplers (1), (12) and (13). Further, the oil-soluble cyan couplers are dissolved as oil-protected type couplers in high boiling point organic solvents and may be dispersed and incorporated into silver halide photographic emulsions. Examples of the cyan couplers belonging to this type are the aforesaid couplers (2), (3), (4), (5), (6), (7), (8), (9), (10), (11), (16), (17), (18) and (19).

For incorporation into light-sensitive silver halide photographic materials of, for example, the oil-protected type cyan couplers among those of the present invention, there may be adopted any of the known procedures. For example, one or more of the cyan couplers are dissolved in one, or if necessary both, of a high boiling point solvent having a boiling point of more than 175° C. such as tricresyl phosphate or dibutyl phthalate, and a low boiling point solvent such as butyl acetate or butyl propionate. Thereafter, the resulting solution is mixed with an aqueous gelatin solution containing a surfactant, and then emulsified by means of a high speed rotary mixer on a colloid mill to form an emulsion. This emulsion is incorporated directly into a silver halide photographic emulsion, which is then coated on a support including glass plates, synthetic resin plates, various film bases, baryta papers and polyethylene laminate papers, and is then dried to remove a major proportion of the low boiling point solvent, whereby a light-sensitive silver halide photographic material can be prepared. Alternatively, the said emulsion is once set, finely cut (extruded into the form of noodles) and subsequently freed from the low boiling point solvent by water-washing or the like means, and the thus treated emulsion is incorporated into said photographic emulsion, which is then coated on said support and dried, whereby a light-sensitive silver halide photographic material can be obtained.

The above-mentioned incorporation procedure is merely an example, and it is needless to say that the manner of incorporation of the cyan coupler of the present invention is not limited to the above.

In the above case, the amount of the cyan coupler to be incorporated into the emulsion is preferably in the range from 10 to 100 g. per mole of the silver halide, in general. However, the amount of said coupler is not always limited to said range, but may be properly varied according to the application purpose of the resulting photographic material. Further, the cyan coupler of the present invention may be incorporated into two or more of different emulsion layers of a multi-layered light-sensitive color photographic material.

The silver halide emulsion used in the present invention may be prepared by use of any silver halide salt such as silver chloride, silver iodobromide or silver chlorobromide, and may contain a chemical sensitizer such as a sulfur sensitizer, a natural sensitizer present in gelatin, a reductive sensitizer or noble metal salts. Further, the emulsion may contain ordinary photographic additives such as, for example, an antifoggant, stabilizer, anti-stain agent, anti-irradiation agent, physical property-improving high molecular weight additive, hardener, coating aid, etc., and may contain as an optical sensitizer any of carbocyanine and merocyanine dyes.

The thus obtained light-sensitive color photographic material is exposed to radiation such as α-rays or β-rays, visible rays or ultraviolet rays, developed with a color developer containing an aromatic primary amine type compound as a developing agent, and then subjected to bleaching, desilvering and fixing to obtain an image containing a high density cyan dye excellent in spectral absorption characteristic and durability and favorable in transparency. The durability of the color image can further be enhanced when the photographic material containing the cyan coupler of the present invention is incorporated with an ultraviolet absorber of the benzophenone type, e.g. 2-hyroxy-4-dodecyloxybenzophenone, or the triazole type, e.g. 2-(2'-hydroxy-3',5'-di-tert-butylphenyl)benzotriazole.

Typical examples of the aromatic primary amine type developing agent used for development in the present invention are sulfates, sulfites and hydrochlorides of N,N-diethyl-p-phenylenediamine, N-ethyl-N-β-methanesulfonamidoethyl-3methyl-4-aminoaniline, N-ethyl-N-hydroxyethyl-p-phenylenediamine, N-ethyl-N-hydroxyethyl-2-methyl-p-phenylenediamine and N,N-diethyl-2-methyl-p-phenylenediamine.

Further, the color developer may contain a development control agent, e.g. citrazinic acid, in addition to the aforesaid developing agent.

The present invention is illustrated in further detail below with reference to examples, but the examples are by way of illustration, and the modes of practice of the invention are, of course, not limited to the examples.

In the examples, such known couplers as shown below were used as control couplers for comparison.

Control coupler (i)

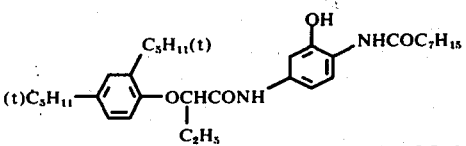

(cf. U.S.P. 2,722,162)

Control coupler (ii)

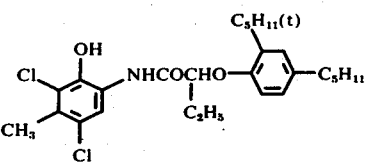

(cf. U.S.P. 2,423,730)

Control coupler (iii)

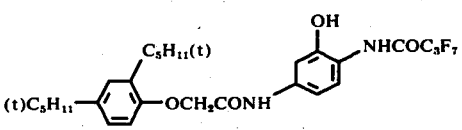

(cf. U.S.P. 2,895,826)

Control coupler (iv)

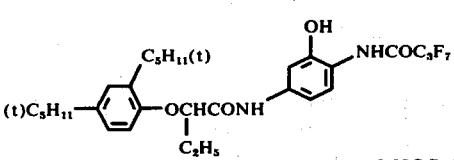

(cf. U.S.P. 2,895,826)

EXAMPLE 1

10 Grams of each of the couplers (4) and (5) and the control couplers (i), (ii), (iii) and (iv) was completely dissolved at 60° C. in a mixture comprising 20 ml. of dibutyl phthalate and 60 ml. of ethyl acetate. This solution was mixed with 5 ml. of a 10% aqueous solution of Alkanol B (alkylnaphthalene sulfonate, commercially available from Du Pont Co.) and 20 ml. of a 5% aqueous gelatin solution, and the resulting mixture was emulsified by use of a colloid mill to prepare a dispersion of each coupler.

Subsequently, each coupler dispersion was added to 500 g. of a high speed negative, gelatinous silver iodobromide emulsion (containing 6 mole% of silver iodide), which was then coated on a cellulose triacetate film base and dried to obtain six kinds of photographic materials each having a stable coating film which were designated Sample Nos. (1) to (6).

After exposure through an optical wedge, each sample was subjected to color development at 20° C. for 10 minutes, using a color developer of the following composition:

| Composition of the color developer: | |
|---|---|
| N-Ethyl-N-β-methanesulfonamidoethyl-3-methyl-4-aminoaniline sulfate | 5.0 g. |
| Anhydrous sodium sulfite | 2.0 g. |
| Sodium carbonate (monohydrate) | 50.0 g. |
| Potassium bromide | 1.0 g. |
| Sodium hydroxide | 0.55 g. |

| | |
|---|---|
| Benzyl alcohol | 4.0 g. |
| Water to make | 1,000 ml. |

Subsequently, the developed sample was subjected to ordinary stopping (for 2 minutes), fixing (for 5 minutes) and water-washing (for 10 minutes), and then bleached for 5 minutes with a bleaching solution of the following composition:

| Composition of the bleaching solution: | |
|---|---|
| Potassium ferricyanide | 100 g. |
| Potassium bromide | 50 g. |
| Water to make | 1,000 ml. |

Thereafter, the sample was subjected to water-washing for 5 minutes, and then fixed at 20° C. for 5 minutes with a fixing solution of the following composition:

| Composition of the fixing solution: | |
|---|---|
| Sodium thiosulfate (pentahydrate) | 250 g. |
| Water to make | 1,000 ml. |

The sample was again subjected to water-washing for 25 minutes, and then dried to form a cyan colored image.

The cyan dye image formed in each sample was measured in speed, maximum density (Dmax), absorption maximum wavelength ($\lambda$ max) and fastness to light, heat and humidity. The results obtained were as set forth in Table 1.

In the table, the speed was represented by a relative value measured by assuming as 100 the speed of the sample (6). Further, the light fastness was represented by the percentage to the density of untreated dye of the density of residual dye after treating the sample for 16 hours by use of a Xenon Fade-O-Meter, and the heat-humidity fastness was represented by the percentage to the density of untreated dye of the density of residual dye after incubating the sample for 2 weeks under the conditions of 50° C. and 80%RH.

there was difficulty in dissolving said coupler in the solvents, but also the cyan dye image resulting therefrom was opaque with turbidity.

EXAMPLE 2

The same six kinds of samples as in Example 1 were individually exposed through an optical wedge, and then subjected to color development at 38° C. (for 3 minutes and 15 seconds), bleach-fixing (for 6 minutes), water-washing (for 2 minutes) and stabilization bath treatment (for one minute and 30 seconds) to investigate the influence derived from the difference in manner of development treatment. As a result, it was confirmed that the photographic properties of the cyan dye image formed in each sample were the same as in Example 1.

The compositions of the color developer and bleach-fixing solution used in this example were as follows:

| | |
|---|---|
| Composition of the color developer: | |
| N-Ethyl-N-($\beta$-hydroxyethyl)-3-methyl-4-aminoaniline hydrochloride | 5.0 g. |
| Anhydrous sodium sulfite | 2.0 g. |
| Sodium carbonate (monohydrate) | 50.0 g. |
| Potassium bromide | 1.0 g. |
| Sodium hydroxide | 0.55 g. |
| Water to make | 1,000 ml. |
| Composition of the bleach-fixing solution: | |
| Iron ammonium ethylenediamine-tetraacetate | 45 g. |
| Ammonium thiocyanate | 10 g. |
| Anhydrous sodium sulfite | 10 g. |
| Ammonium thiosulfate | 60 g. |
| 2-Ammonium ethylenediamine-tetraacetate | 5 g. |
| Water to make | 1,000 ml. |

EXAMPLE 3

10 Grams of each of the couplers (3) and (6) and the control coupler (i) was completely dissolved at 60° C. in a mixture comprising 20 ml. of tricresyl phosphate and 60 ml. of ethyl acetate. This solution was mixed with 5 ml. of a 10% aqueous solution of Alkanol B and 20 ml. of a 5% aqueous gelatin solution, and the resulting mixture was emulsified by use of a colloid mill to prepare a dispersion of each coupler.

Table 1

| Sample No. | Coupler | Speed | Gamma | Dmax | $\lambda$ max (m$\mu$) | Fastness Light fastness | Fastness Heat-humidity fastness |
|---|---|---|---|---|---|---|---|
| 1 | Coupler (4) | 119 | 1.20 | 2.25 | 669 | 94 | 93 |
| 2 | Coupler (5) | 120 | 1.22 | 2.31 | 670 | 95 | 94 |
| 3 | Control coupler (i) | 125 | 1.20 | 2.25 | 645 | 85 | 83 |
| 4 | Control coupler (ii) | 105 | 1.03 | 2.15 | 667 | 88 | 61 |
| 5 | Control coupler (iii) | 98 | 0.88 | 2.00 | 670 | 92 | 90 |
| 6 | Control coupler (iv) | 100 | 0.92 | 2.08 | 670 | 92 | 89 |

As is clear from Table 1, Samples 1 and 2, in which had been used the cyan couplers of the present invention, gave cyan dye photographic images which were superior in photographic properties to the other samples, in which had been used the control couplers. Moreover, the images of the Samples 1 and 2 were quite clear and were excellent in transparency.

In contrast, the control coupler (iii), in particular, was not only low in solubility in organic solvents and Subsequently, each coupler dispersion was added to a red-sensitive high speed silver iodobromide emulsion (containing 4 mole% of silver iodide), which was then coated on a cellulose acetate film base and dried to obtain three kinds of photographic materials each having a stable coating film which were designated Sample Nos. (7) to (9).

After exposure through an optical wedge, each sample was first developed at 21° C. for 12 minutes, using a developer of the following composition:

| Composition of the developer: | |
|---|---|
| Metol | 3.0 g. |
| Anhydrous sodium sulfite | 50.0 g. |
| Hydroquinone | 6.0 g. |
| Sodium carbonate | 40.0 g. |
| Potassium bromide | 3.5 g. |
| Potassium thiocyanate | 2.0 g. |
| Water to make | 1,000 ml. |

Subsequently, the developed sample was subjected to stopping, film-hardening and water-washing treatments according to ordinary procedures, thereafter to secondary exposure by use of a white light, and then to color development at 21° C. for 13 minutes, using a color developer of the following composition:

| Composition of the color developer: | |
|---|---|
| N,N-Diethyl-2-methyl-p-phenylenediamine | 3.0 g. |
| Anhydrous sodium sulfite | 4.0 g. |
| Sodium carbonate | 20.0 g. |
| Potassium bromide | 2.0 g. |
| Water to make | 1,000 ml. |

Thereafter, the sample was subjected to stopping, water-washing, bleaching and fixing treatments according to ordinary procedures, washed with running water for 20 minutes and then dried to form a cyan dye positive image.

The cyan dye image formed in each sample was measured in speed, Dmax, λmax and fastnesses to light and to heat-humidity. The results obtained were as set forth in Table 2.

In the table, the speed was represented by a relative value measured by assuming as 100 the speed of the sample 9, and the fastnesses were represented by percentages measured in the same manner as in Example 1.

Table 2

| Sample No. | Coupler | Speed | Dmax | λmax | Fastness Light fastness | Heat-humidity fastness |
|---|---|---|---|---|---|---|
| 7 | Coupler (3) | 113 | 2.23 | 675 | 94 | 92 |
| 8 | Coupler (6) | 116 | 2.30 | 675 | 95 | 93 |
| 9 | Control coupler (ii) | 100 | 2.16 | 670 | 89 | 62 |

As is clear from Table 2, the cyan dye positive images formed in the samples 7 and 8, in which the cyan couplers of the present invention had been used, were more excellent particularly in heat-humidity fastness than the cyan image formed in the sample 9, in which the control coupler had been used, and the images were quite clear and were favorable in transparency.

EXAMPLE 4

A high speed silver iodobromide emulsion (containing 5 mole% of silver iodide) was coated on a polyester film base and then dried to prepare a light-sensitive photographic material having a single emulsion layer. This photographic material was exposed through an optical wedge, and then subjected to color development at 24° C. for 3 minutes, using an external type color developer of the below-mentioned composition which had been incorporated with the coupler (1).

| Composition of the color developer: | |
|---|---|
| N,N-Diethyl-2-methyl-p-phenylenediamine | 2.0 g. |
| Anhydrous sodium sulfite | 2.0 g. |
| Sodium carbonate (monohydrate) | 20.0 g. |
| Potassium bromide | 1.0 g. |
| Coupler (1) | 2.0 g. |
| Water to make | 1,000 ml. |

Subsequently, the sample was washed with water for 4 minutes, treated with an ordinary bleaching bath for 5 minutes, washed with water for 5 minutes, fixed for 5 minutes, washed with water for 30 minutes and then dried to obtain a highly transparent cyan dye image having such excellent spectral absorption characteristic as an absorption maximum of 668 mμ.

What is claimed is:

1. A process for forming a cyan dye photographic image, which comprises bringing a monohydro-polyfluoroalkylcarbonamido compound of the formula

A — NHCO(CF$_2$CF$_2$)$_n$H wherein A is a phenolic or naptholic cyan coupler residue and n is a positive integer of 1 to 7, into contact with exposed silver halide crystals in the presence of an aromatic primary amine type color developing agent for said silver halide crystals.

2. A light-sensitive silver halide photographic material having a support and coated thereon a light-sensitive silver halide emulsion layer containing as a cyan coupler a compound having a monohydro-polyfluoroalkylcarbonamido group, said compound being represented by the formula

A — NHCO(CF$_2$CF$_2$)$_n$H wherein A is a phenolic or naphtholic cyan coupler residue and n is a positive integer of 1 to 7.

3. A color developer for developing exposed light-sensitive silver halide color photographic material, which comprises an aromatic primary amine type color developing agent and a compound having a monohydro-polyfluoroalkylcarbonamido group, said compound being represented by the formula

A — NHCO(CF$_2$CF$_2$)$_n$H wherein A is a phenolic or naphtholic cyan coupler residue and n is a positive integer of 1 to 7.

* * * * *